(12) United States Patent
Wiegand

(10) Patent No.: US 8,746,146 B1
(45) Date of Patent: Jun. 10, 2014

(54) BULLET OR SLUG WITH BLOOD-TRAIL ENHANCER

(71) Applicant: Gayle Wiegand, Queen Creek, AZ (US)

(72) Inventor: Gayle Wiegand, Queen Creek, AZ (US)

( * ) Notice: Subject to any disclaimer, the term of this patent is extended or adjusted under 35 U.S.C. 154(b) by 0 days.

(21) Appl. No.: 13/754,159

(22) Filed: Jan. 30, 2013

Related U.S. Application Data

(63) Continuation-in-part of application No. 13/526,577, filed on Jun. 19, 2013.

(51) Int. Cl.
*F42B 5/145* (2006.01)
*F42B 12/36* (2006.01)
*F42B 12/46* (2006.01)

(52) U.S. Cl.
USPC ............................. 102/513; 102/517

(58) Field of Classification Search
USPC .......................... 102/501, 512, 513, 516, 517
See application file for complete search history.

(56) References Cited

U.S. PATENT DOCUMENTS 7,255,659 B2 * 8/2007 Jones ........................... 473/583
7,426,888 B2 9/2008 Hunt \* cited by examiner

*Primary Examiner* — James Bergin
(74) *Attorney, Agent, or Firm* — Bernhard P. Molldrem, Jr.

(57) ABSTRACT

A bullet or slug for hunting a game animal is fitted with a capsule that contains an effective quantity of a blood trail enhancer. The latter is composed of fish oil and apple cider vinegar together with effective amounts of natural anti-coagulant agents, such as ginger, onion, and garlic. The fish oil and apple cider vinegar also serve as anti-coagulants. These agents including also are effective in promoting healing of a non-fatal wound in a game animal.

10 Claims, 1 Drawing Sheet

BULLET OR SLUG WITH BLOOD-TRAIL ENHANCER

This is a continuation-in-part of my copending patent application, U.S. Ser. No. 13/526,577, filed Jun. 19, 2012, the contents whereof are incorporated herein by reference.

FIELD OF THE INVENTION

The present invention relates generally to hunting for game, such as deer or the like, and is more particularly directed to a composition, and to a technique for applying the composition to a projectile that is fired at the game animal, so as to inhibit coagulation of blood from the wound caused by the projectile, so that the blood trail left when the game animal is wounded but bounds off will continue and increase the probability that the hunter will locate the animal and harvest it. The invention is also concerned with all-natural compositions so that if the wound is not fatal to the game animal, and the animal escapes, the probability increases that the animal's wound will heal and not become infected.

BACKGROUND OF THE INVENTION

Hunting is widely enjoyed, especially hunting for game animals such as white-tail deer. A proficient hunter using a rifle, shotgun (with slug), or a muzzle-loading long gun, will aim so as to strike the deer (or other game animal) in a vital area, so that the shot fired creates a mortal wound and the deer dies quickly. However, the deer often escapes, even after a fatal wound, and can run for a considerable distance to seek cover somewhere in the underbrush. In that case, the hunter attempts to follow the blood trail left behind as the wounded animal moves, so the hunter can find the deer and harvest it properly.

In hunting, the results of a shot of a projectile (bullet, slug or arrow) at an animal can be classified in four basic types. (1) In a clean miss, where the shot misses the animal, the deer bounds away unwounded, and the hunt for that particular animal is at an end. (2) For a clean kill shot, i.e., where the shot is well placed in a vital organ, the wound results in an adequate blood trail which leads the hunter easily to the animal, which expires quickly from the wound. (3) A typical kill shot that is a less than a perfectly placed shot, will result in a wound with a blood trail that will eventually dry up before leading to the animal, which will eventually expire from the wound. Every year there are thousands of deer that are killed this way, and where the hunter has to abandon the search after having spent hours trying in vain to find the animal, because the blood trail has ended before the deer can be located. (4) A non-vital shot is one that misses any vital organs, but nonetheless wounds the animal, i.e., in the rump or shoulder, for example, and where the wound, while not fatal in itself, can become infected and/or fail to heal properly. This can cause undue stress or eventually death to the animal, but will not result in harvesting of the animal by any hunter. All or nearly all hunters have experienced, or eventually will experience, a shot on a game animal that they know is not fatal, leaving the hunter hoping that the wounded animal survives and recovers, although often the wounded animal does succumb to the infection.

Some previous attempts to increase the blood flow from the wound on a game animal have been proposed, but more particularly for archery or bowhunting. These have involved modifying arrows to increase the wound size or hold the wound open. However, these techniques involve having to use special, modified arrows or arrowheads, and cannot guarantee any success if the arrow penetrates too far or not far enough. They also have limited applicability to hunting with a gun. A previous attempt to provide a blood-clot-inhibiting formulation that was to be applied to blades of an arrow head is described in Jones U.S. Pat. No. 7,255,659. The Jones formulation was an aqueous mixture of gums and glycerine, with its active ingredient being trisodium citrate, with small inclusions of tumeric, white willow bark, ginger and fenugreek. While the formulation was intended to inhibit blood clotting, it is unknown just how much longer blood would continue to flow from any wound where the Jones formulation was present. Also, the Jones formulation was not intended to promote healing or prevent infection in the event of a non-mortal hit of an animal, nor is there any indication that the ingredients in that formulation would have sufficient effectiveness in healing a wounded animal that escapes with such a wound. Furthermore, there was no provision for applying an effective blood anti-clot preparation or blood-trail enhancer onto a bullet or slug or any other explosive-powered projectile used in hunting.

OBJECTS AND SUMMARY OF THE INVENTION

It is an object of the present invention to provide blood trail enhancer that can be employed on or in a bullet or shotgun slug, and which will significantly slow the processes that cause blood trails to dry up.

It is another object to provide a blood trail enhancer in combination with a bullet or shotgun slug that delivers natural healing and anti-infection agents to the wound in the event of a less than mortal shot.

It is a further object to provide a blood trail enhancer treatment that can be embedded in a bullet or slug as a part of the projectile, so that it does not have to be applied in the field.

In accordance with an aspect of the present invention, the blood trail enhancer is a composition of all-natural ingredients, including fish oil and apple cider vinegar, together with lesser amounts of ingredients that are both known anti-coagulants and known healing agents, such as garlic, onion, ginger, papaya, etc. The included ingredients are natural blood thinners, and/or natural anti-coagulants, and/or natural platelet inhibitors, and are also natural ingredients that promote healing and fight infections. It is desired to avoid synthetic ingredients, sedatives, muscle relaxants, or anaesthetic materials, as they may present health problems, if present in the meat that is later harvested from the animal.

The composition can be contained in a small plastic capsule that is or can be embedded within a cavity in the projectile, i.e, the hollow nose of a hollowpoint bullet or slug, and designed so as to tear open on impact and distribute the composition about the flesh at the point of entry of the bullet or slug.

According a to more particular aspect, the composition of the invention comprises fish oil and apple cider vinegar in respective amounts of 45 to 55 parts per hundred by volume and 25 to 35 parts per volume of the composition, and additional natural ingredient that inhibits blood clotting and promotes healing, in 5 to 10 parts by volume each of garlic, onion, and ginger. Papaya may also be used in some cases.

Some successful blood trail enhancers, which prolong the time before clotting up to fifteen to twenty minutes, can be formulated as follows (in amounts by volume):

a. fish oil—50; apple cider vinegar—30; garlic—10; onion—5; and ginger—5.

b. fish oil—47; apple cider vinegar—33; garlic—9; onion—6; and ginger—5.

c. fish oil—45; apple cider vinegar—35; garlic—10; onion—5; and ginger—5.

This same composition can be applied to the arrows and arrowheads in advance of hunting and allowed to dry, or it can be applied to the arrows in the field. In this case, it is preferred that the composition be contained in a plastic capsule in a cavity in the nose of the bullet or slug. In either event, the composition, when used with the projectile will allow the hunter to find the killed or wounded deer or large game animal by the enhanced blood trail. Also, there will be a much better survival rate, i.e., better healing and infection fighting, for non-mortally wounded animals.

DETAILED DESCRIPTION OF THE PREFERRED EMBODIMENT(S)

Figure 1:
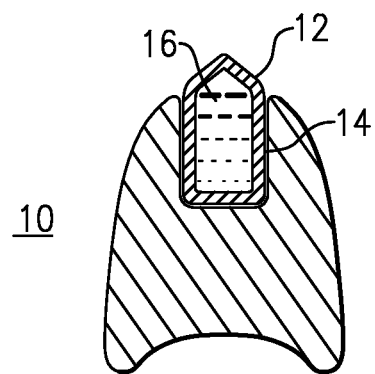
FIG. 1 is a cross section of a bullet including a capsule containing the blood trail enhancer of this invention.

The blood trail enhancer that I have formulated is composed of natural blood thinners and natural anti-pathogens including fish oil and apple cider vinegar, plus other ingredients including powdered ginger, powdered onion and powdered garlic, each of which has a strong anti-coagulant effect as well as an anti-pathogen effect. Other possible natural ingredients may be used, but not all combinations of ingredients mix well while other possible combinations may not achieve sufficient anti-coagulant effectiveness.

The protocol that was followed for testing the effectiveness of various formulations of the blood trail enhancer is that which is described in Hattersley, Paul G., *Activated Coagulation Time of Whole Blood*, Journal of the American Medical Association, May 2, 1966, page 150, ff., which is incorporated herein by reference. The Hattersley publication describes the protocol for measuring the active coagulation time (ACT) of whole blood, and involves drawing a small amount (1 ml) of blood (and other tissue juices) into a glass tube that contains diatomaceous earth, the tube being pre-warmed to body temperature (e.g., 37° C.), and starting a timer when blood appears in the tube. The tube is then tilted at five-second intervals, and is checked visually until the first unmistakable clot appears. For normal blood where no anti-clotting agents are present, this time will typically be between one and two minutes. For human patients who are administered blood thinners, the time may exceed two minutes, but usually will not exceed two minutes, thirty seconds.

This technique was used here to test coagulation of fresh blood in the presence of the agents that constitute the natural ingredients and that include compositions formulated as the preferred blood trail enhancers, as detailed below.

In compositions as tested in which there was significant delay in clotting, fish oil was present in an amount of between 55 and 70 parts per hundred, apple cider vinegar or ACV was present in an amount between 25 and 40 parts per hundred, and the balance was composed of the additional natural ingredients (i.e., ginger, garlic, onion, papaya, or the like).

First, the ACT was timed for blood (as a control) and then for blood in contact with each individual ingredient, with the results as follows:

| Test no. | Substance | Time (ACT) |
|---|---|---|
| 1 | Control | 1:48 (min:sec) |
| 2 | Papaya | 2:10 |
| 3 | Garlic liquid | 6:37 |
| 4 | Ginger liquid | 2:20 |
| 5 | Fish Oil | 3:30 |
| 6 | Onion powder | 2:50 |
| 7 | Garlic powder | 3:47 |
| 8 | Ginger powder | 3:00 |
| 9 | mix of all ingredients | 15+ minutes ** |

The protocol as described in the Hattersley article was followed in each test run. (** Note: when all ingredients were combined together and contacted with the blood sample in test 9, clotting was not detected after 15 minutes when the test was terminated.)

Subsequent to the above test runs, batches of the blood trail enhancer were prepared composed as follows, and each was contacted in turn with a blood sample, and the ACT was measured according to the Hattersley protocol. One drop of the composition was contacted with the blood in each test (except the Control).

Control: (blood alone); ACT=1:45;

Example I: Fish oil—70; garlic—10, ginger—10, onion—10 (parts per hundred); ACT=2:00;

Example II: Fish oil—80; garlic—10; ginger—5; onion—5; ACT=2:00.

Example III: ACV—80; Garlic—10; ginger—5; onion—5 (no fish oil); ACT=2:30;

Example IV: ACV—40; fish oil—40; garlic—10; ginger—5; onion—5; ACT=2:00;

Example V: ACV—45; fish oil—45; garlic—5; onion—5 (no ginger); ACT=3:08;

Example VI: ACV—30, fish oil(1)-50, garlic—10, onion—5, ginger—5; ACT=15:20;

Example VII: ACV—30; fish oil(2)-50; garlic—9; onion—6; ginger—5: ACT=20 minutes+.

(Notes: (1) in Example VI, a triple-strength pharmaceutical grade fish oil was used. (2) in Example VII, a pet grade fish oil was used, which had no flavorants or additives.)

Example VIII: ACV—33; fish oil (pet grade)—47; garlic—9; onion—6; ginger—5; ACT=20 minutes+;

Example IX: ACV—35; fish oil (pet grade)—45; garlic—10; onion—5; ginger—5; ACT=20 minutes+.

In the particularly effective compositions, namely, VI through IX, there was little odor to the composition after drying. These compositions seemed to mix well and seemed easy to dispense.

Because of the effect as described above on whole blood in a test situation, it is expected that there would be a similar prolonging of free blood flow from the wound when an animal suffers a mortal hit, and there would be adequate blood trail in most cases to lead the hunter to the game animal so it could be successfully harvested. The all natural ingredients also promote healing of the wound in the event the hit is not fatal, and also inhibit or combat infection from various pathogens, increasing the likelihood the animal will recover and survive after a non-lethal wound.

FIG. 1 shows one possible embodiment of the invention in which a bullet 10 has a capsule 12 contained in a cavity 14 in the nose of the bullet 10. The bullet may be included in a cartridge (not shown) for normal rifle hunting, or may be designed to be used in a muzzle loading rifle. The included capsule 12 contains an effective amount of the blood-trail enhancer preparation 16, described just above. This bullet 10 is a hollow-point bullet, and its front end or nose tends to spread our laterally, or petal out, upon impact. This action also shatters the capsule 12 and distributes the blood trail enhancer at the wound site. In the event of a fatal shot, the animal's blood will be inhibited from clotting and will leave a better-defined blood trail that will lead the hunter to the location of the animal when the wounded animal walks or runs off for a limited distance. In the event of a non-fatal wound, the ingredients of the preparation will help healing and prevent infection, so that the animal is more likely to survive the wound.

Figure 2:
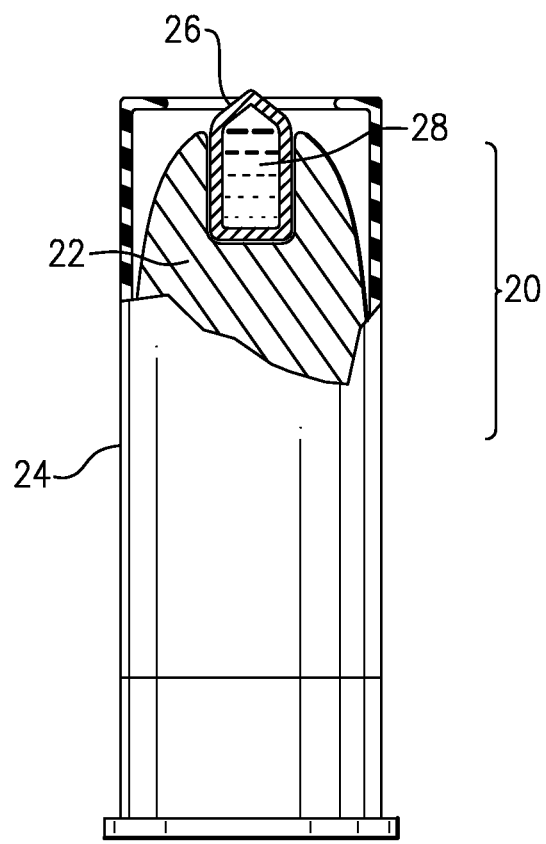
FIG. 2 illustrates a shotgun cartridge or shell with a shotgun slug that includes a capsule of the blood trail enhancer of this invention.

FIG. 2 shows an example of a shotgun load 20, including a deer slug 22 contained within a shell casing 24, here shown partly cut-away. The slug 22 has body with a hollow nose, i.e., a cavity 26 at its distal end, in which a blood-trail-enhancer-containing capsule 28 is located. This capsule 28 serves the same purpose as the capsule 12 described just above. The slug itself can be of any of a variety of designs, with or without a sabot.

In these and other embodiments the capsule is a hollow vessel made of a suitable plastic or polymer, and is molded or cast so as to fit snubly into the hollow nose or tip of the projectile. The capsule has a wall that is durable enough to contain the blood trail enhancer until after the round is fired, but will split or shatter on impact with the target.

The bullet or slug can also be designed to be used with a compressed-air fired gun, i.e., air gun, where legal.

While the invention has been described in terms of a preferred composition and preferred modes of use, it should be appreciated that the invention is not limited to specific examples, but should be considered broadly, as defined in the appended claims.

I claim:

1. A bullet or slug for hunting of game animals and intended to be fired from a gun at a game animal, the bullet or slug comprising a body having a cavity therein, and a capsule fitted into said cavity and designed to shatter upon impact with the game animal, the capsule containing an effective amount of a natural blood trail enhancer composition, to inhibit coagulation of blood at a wound site in a target game animal at a wound caused when the target game animal is struck by said bullet or slug, and also to promote healing and prevent infection at a wound site when the wound is not fatal, the composition comprising:
   fish oil
   apple cider vinegar, and
   an effective amount of at least one additional natural ingredient that inhibits blood clotting and promotes healing, the at least one additional ingredient being selected from the group consisting of ginger, onion, garlic and papaya.

2. The bullet or slug of claim 1 wherein said fish oil and said apple cider vinegar are provided in respective amounts of 45 to 55 parts per hundred by volume and 25 to 35 parts per volume of the composition.

3. The bullet or slug of claim 2, wherein said at least one natural ingredient is provided in 5 to 10 parts by volume each of garlic, onion, and ginger.

4. The bullet or slug of claim 1, wherein the composition is composed in amounts by volume as follows:
   fish oil—50;
   apple cider vinegar—30;
   garlic—10;
   onion—5; and
   ginger—5.

5. The bullet or slug of claim 1, wherein the composition is composed in amounts by volume as follows:
   fish oil—47;
   apple cider vinegar—33;
   garlic—9;
   onion—6; and
   ginger—5.

6. The bullet or slug of claim 1 wherein the composition is composed in amounts by volume as follows:
   fish oil—45;
   apple cider vinegar—35;
   garlic—10;
   onion—5; and
   ginger—5.

7. A method of hunting with a rifle or shotgun of a target game animal employing one or more fired projectiles in the nature of a bullet or slug that has a hollow cavity at its nose, the method comprising:
   applying into said hollow cavity of the bullet or slug a capsule containing an effective a composition to inhibit coagulation of blood of the target game animal and also to promote healing of a wound caused by the bullet or slug when the wound is not fatal, the capsule being designed to shatter upon impact with the target game animal so as to distribute the contained composition about the flesh of the animal at the vicinity of the wound caused by the bullet or slug, the composition including fish oil in an amount of 45 to 55 parts per hundred by volume;
   apple cider vinegar in an amount of 25 to 35 parts per hundred by volume;
   and the balance composed of additional natural ingredients with blood-coagulation inhibiting properties and natural healing properties, namely, between five and fifteen parts per hundred by volume of garlic, onion, and ginger; and
   launching one or more of said projectiles at said target game animal.

8. The method of hunting of claim 7 wherein said composition is composed in amounts by volume as follows:
   fish oil—50;
   apple cider vinegar—30;
   garlic—10;
   onion—5; and
   ginger—5.

9. The method of hunting of claim 7 wherein said composition is composed in amounts by volume as follows:
   fish oil—47;
   apple cider vinegar—33;
   garlic—9;
   onion—6; and
   ginger—5.

10. The method of hunting of claim 7 wherein said composition is composed in amounts by volume as follows:
   fish oil—45;
   apple cider vinegar—35;
   garlic—10;
   onion—5; and
   ginger—5.

* * * * *

UNITED STATES PATENT AND TRADEMARK OFFICE
CERTIFICATE OF CORRECTION

| | | |
|---|---|---|
| PATENT NO. | : 8,746,146 B1 | Page 1 of 1 |
| APPLICATION NO. | : 13/754159 | |
| DATED | : June 10, 2014 | |
| INVENTOR(S) | : Gayle Wiegand | |

It is certified that error appears in the above-identified patent and that said Letters Patent is hereby corrected as shown below:

On the Title Page

Item (63) should read, Continuation in-part of application No. 13,526,577, filed on June 19, 2012.

Signed and Sealed this
Fourth Day of November, 2014

Michelle K. Lee
*Deputy Director of the United States Patent and Trademark Office*